United States Patent [19]
Pitzen

[11] Patent Number: 5,484,387
[45] Date of Patent: Jan. 16, 1996

[54] METHOD AND DEVICE FOR LOOSENING CONNECTIVE TISSUE AND STIMULATING BLOOD CIRCULATION

[75] Inventor: Sylvester A. Pitzen, Phoenix, Ariz.

[73] Assignee: Sono Therapy Institute, Inc., Phoenix, Ariz.

[21] Appl. No.: 289,414

[22] Filed: Aug. 12, 1994

Related U.S. Application Data

[63] Continuation-in-part of Ser. No. 139,634, Oct. 19, 1993, abandoned, which is a continuation of Ser. No. 800,135, Nov. 29, 1991, abandoned, which is a continuation-in-part of Ser. No. 483,405, Feb. 11, 1990, abandoned.

[51] Int. Cl.⁶ .................................................. A61H 7/00
[52] U.S. Cl. ........................ 601/15; 601/12; 607/109
[58] Field of Search .................... 601/12, 15, 18–21, 601/46, 61, 63, 78–81, 155; 604/20; 607/2, 115, 116, 108–111, 145–151; 128/639, 644, 662.03, 734

[56] References Cited

U.S. PATENT DOCUMENTS

| | | |
|---|---|---|
| 1,480,353 | 1/1924 | Wappler . |
| 1,890,270 | 12/1932 | Takaoka ........................... 601/15 X |
| 3,872,859 | 3/1975 | Pitzen et al. . |
| 4,175,551 | 11/1979 | D'Haenens et al. . |

FOREIGN PATENT DOCUMENTS

| | | |
|---|---|---|
| 0107258 | 5/1984 | European Pat. Off. . |
| 2585242 | 1/1987 | France . |
| 938138 | 10/1963 | United Kingdom . |

*Primary Examiner*—Joe H. Cheng
*Attorney, Agent, or Firm*—Robert L. Harrington

[57] ABSTRACT

A massaging electrode is pressed against discrete areas of a subject person's scalp or body and worked from side to side or in a preferred or random massage pattern to thereby move the skin and its underlying layers relative to the underlying area. The electrode is a gold plated phonojack which is encased in silver solder to optimize transmission of electrical current. Electrical current is passed through the electrode and into the subject person's scalp by connecting the electrode to an electrical conductor from an electrical current generating device which generates oscillating voltage to the pad in a low range and at a variation of voltages. The ground contact is hand held by the subject person so that electrical current is directed down through the skin layers during the massaging process.

6 Claims, 4 Drawing Sheets

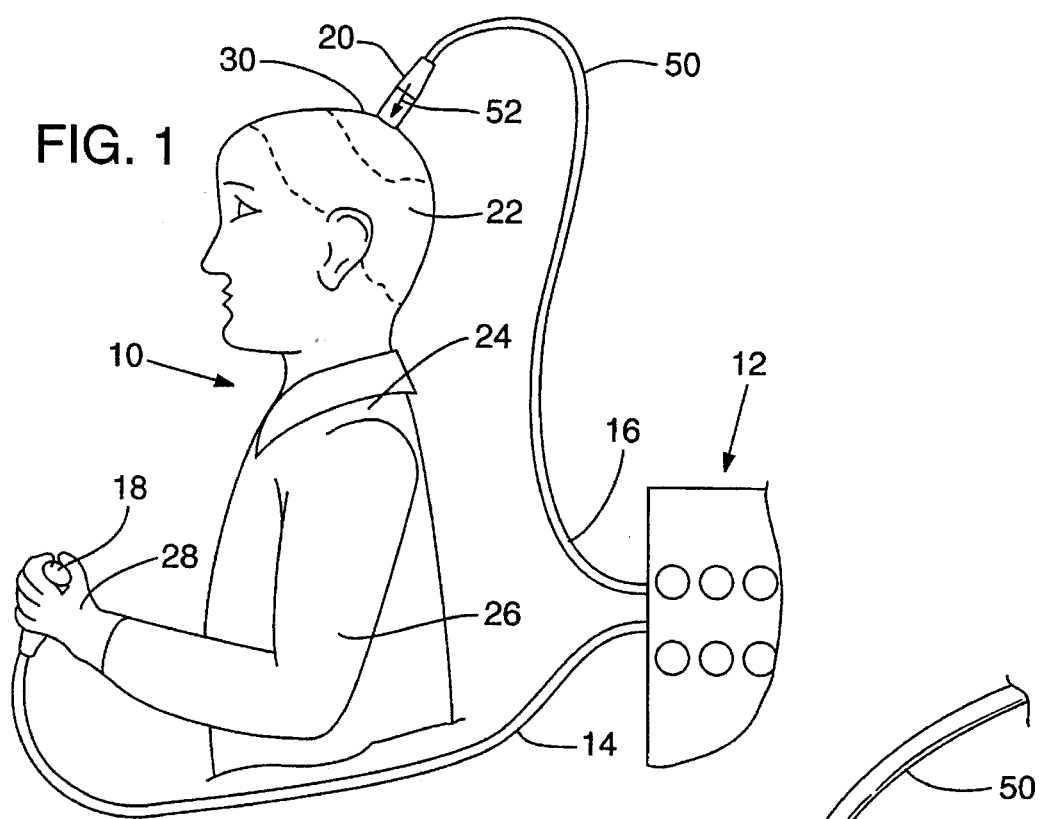
FIG. 1
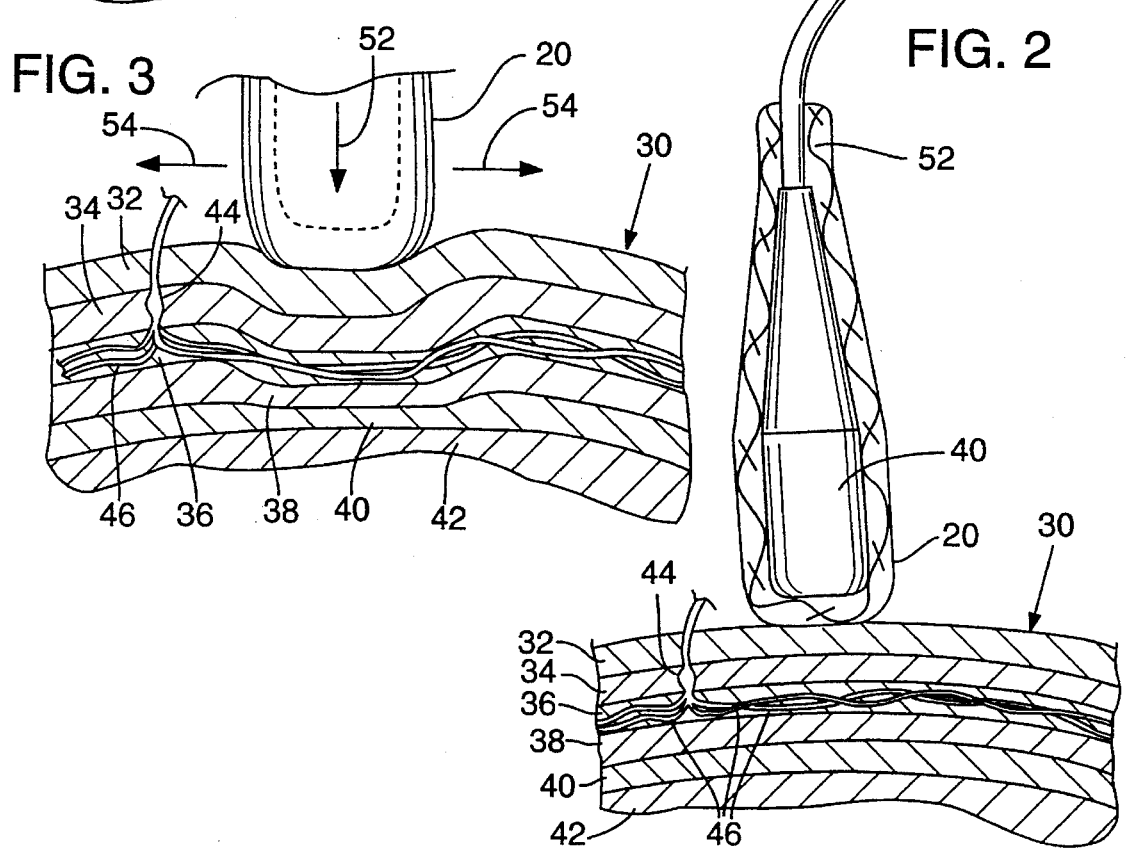
FIG. 2
FIG. 3

The present application is a continuation-in-part of U.S. patent application Ser. No. 08/139,634 filed Oct. 19, 1993, now abandoned, which was a continuation of Ser. No. 07/800,135 filed Nov. 29, 1991 (abandoned) which was a continuation-in-part of U.S. patent application Ser. No. 07/483,405 filed Feb. 11, 1990 (abandoned) by the inventor herein Sylvester A. Pitzen of Phoenix, Ariz. and assigned in common to the assignee of the present invention Sono Therapy Institute, Inc. of Arizona.

FIELD OF THE INVENTION

This invention primarily relates to a method and device for loosening connective tissue and stimulating blood circulation particularly beneficial in the rejuvenation of the human scalp as an aid to establishing or improving the conditions associated with hair growth.

BACKGROUND OF THE INVENTION

Hair loss resulting in male-pattern-baldness has come to be accepted as a fact of life in a large percentage of men and women. Attempts at finding a solution to male-pattern-baldness are almost endless. Even though many have claimed to have solved the problem, in whole or in part, there has yet to be found a solution that will truly reverse the process of hair loss resulting in male-pattern-baldness.

The present invention resulted from a practical analysis of the conditions that caused hair loss. In general, hair is generated out of hair roots and follicles that are rooted within the several skin layers that overlie the skull bone. Arteries and veins within these multiple skin layers, which are also comprised of connective tissue and nerves, provide blood supply to the hair roots and follicles which is necessary for the follicles to remain elongated and maintain hair growth the condition associated with. When there is an increase in connective tissue cross-linkage and blood supply is restricted, the follicle shortens and hair the condition associated with growth stops. Each hair on a person's scalp has a short life cycle. A full head of hair is generally evidence that the follicles are actively producing hair. As blood supply and natural nourishment to the follicles begins to wane, so too does the condition associated with hair growth process and male-pattern-baldness rapidly develops.

The analysis now shifts to the question as to what causes the reduction of blood supply to the hair root and follicles of a person's scalp, why does hair loss follow genetic patterns, why does hair loss assume different patterns on different persons, why is it prevalent in men over women, and why does it typically (but not always) begin developing in males in the early to mid-twenties.

The answers to all of these questions are believed provided by a consideration of the scalps of persons who develop male-pattern-baldness versus those who do not. From studies of numerous case histories and the results from extensive testing of the concept embodied in the present invention, it is theorized that male-pattern-baldness largely develops from a combination of four factors.

First is the vascular make-up of the individual. It is known that some individuals have better blood circulation than others. One person may practice horrendous eating and/or grooming habits and never have a blood circulation problem whereas those same habits will cause serious problems for other persons. An individual who naturally tends to have poor blood circulation may be a likely candidate for male-pattern-baldness.

Second is the physical structure of a person's scalp. A person having a "tight" scalp will tend to have skin that is more taut across the top of the scalp. This condition coupled with the aging process and stress causes non-elasticity in the scalp tissue resulting from increased cross-linkage of connective tissue. Different parts of the scalp will have different degrees of tightness depending on the shape of the skull. As will be explained hereinafter, skin that is taut over the skull will more likely experience non-elasticity and a general breakdown of the subcutaneous fat and restriction of the natural nutritional process including nerve stimulation and blood flow, all of which otherwise "feeds" the hair root and follicle.

The third factor is aging. Skin, like all other organs of the body, goes through an aging process. During the first 10–15 years, from birth to adolescence, a person's skin is growing and is very pliable. As maturity sets in, the skin starts to lose elasticity. In those persons where blood circulation in the scalp is more likely to be restricted genetically, where shape of the skull is more likely to induce a tightness of the skin, and where hair follicles are simply not as elongated or healthy; as aging sets in, the elasticity of the skin is reduced, connective tissue becomes dense, blood circulation to the hair root and follicle is further restricted, and the condition associated with hair growth is slowed or inhibited.

The fourth factor is testosterone. It is generally recognized in the scientific community that the male characteristic hormone, testosterone, plays a role in male-pattern-baldness. The exact role this chemical plays in the balding process is not yet clear; however, it is a factor which must be acknowledged and overcome to prevent or retard hair loss.

The present invention is an improvement of the method and device disclosed in U.S. Pat. No. 3,872,859. The concepts explained in that patent are largely applicable to the present invention. The precept of that invention as well as the present invention is that hair root and hair follicles are not created by either the invention of that patent or the present invention. The aging process is not reversed nor is the bone structure or genetic make-up altered in any respect. To the extent that the hair roots and hair follicles are dormant as a result of increased density of connective tissue, inadequate blood circulation, and the presence of testosterone which in turn may be the result of heredity, aging, gender, shape of skull and skin tightening, the condition associated with hair growth can be rejuvenated by loosening, with massage and electrical impulse stimulation, the skin layers that overlie the skull and in which the blood vessels subcutaneous fat and other nutritional processes along with hair follicles reside.

Previously, limited success was experienced through the application of low voltage electrical stimulation of the skin layers of the scalp coupled with massage, as explained in the above-mentioned patent. However, this success was limited in that many treatments over a long period of time were required. In many cases, the treatment was only able to retard hair loss and in others provided little or no increase in the condition associated with hair growth rejuvenation. A significant number of cases did, however, experience rejuvenated the condition associated with hair growth which proved to the inventor that the adopted precept as explained above was valid. It is believed that the lack of success was a result of an improper range of electrical impulses and a need for refinements to the massage technique(s). The aging process is ongoing and in those subjects where deterioration of follicle elongation and/or blood circulation outpaced the rejuvenation process, failure was eminent.

Whereas the primary focus of the invention is directed to stimulation of the condition associated with hair growth, the loosening of connective tissue and improved blood circulation is found to have benefits for other physical impairments as well. Injuries or disease affecting body tissue may similarly reduce elasticity of tissue and create blood circulation problems. As reported in the *New Scientist Journal*, May 17, 1979 issue:

> "If a tensional stress is imposed on connective tissue over a long period, the fibroblasts which make up most of its bulk orient themselves along the lines of stress and begin to multiply more rapidly. They produce more collagen, the fibrous infrastructure of connective tissue. The extra fibers reduce the elasticity of the tissue. As collagen is fairly resistant to enzyme breakdown, these changes tend to be irreversible. The extra fibers take up space in the connective tissue of the muscle, and begin to encroach on the space normally occupied by nerves, blood and lymph vessels. As a result of this crowding, the tissue loses its elasticity and sometimes becomes painful when the muscle is set to work. The required work might then be attempted via another region of tissue, and the useful life of that region would be limited."

Applying the methods discussed herein to injured areas of the body has been found to improve the healing process. However, benefits are not restricted to human subjects. Where a dog suffering from hip dysplasia was treated, the dog was observed to have freedom of movement not previously noted for many months prior to the treatment.

In general, the benefits of connective tissue loosening and improved blood circulation are endless. Even appearance is improved such as a healthier appearing skin. Scalp and/or facial massage with the technique herein described is considered by some subjects to have provided wrinkle reduction and other cosmetic improvements. The technique, when applied to subjects suffering from various forms of arthritis, has reportedly resulted in improvement in range of motion and comfort in performing tasks which were otherwise painful. These and other yet unknown benefits are likely to result from connective tissue loosening and improved blood circulation generated by the present invention. Another less obvious application may be the treatment of problems that develop in space travel. Recent reports on the hazards of space travel suggest that inhibited red blood cell production and reduced muscle resistance may be a serious problem with persons spending long periods in a condition of weightlessness. The present invention or improvements or modifications thereto may provide the answer.

The following disclosure will discuss the invention as applied to hair simulate the condition associated with growth but the reader will appreciate its application to other areas of the body for improving the condition of connective tissue and blood circulation.

BRIEF SUMMARY OF THE PRESENT INVENTION

The present invention is an improvement over the method and apparatus disclosed in U.S. Pat. No. 3,872,859. Low voltage stimulation and simultaneous massage are believed to still be the key factors for achieving nerve stimulation and loosening the skin layers and connective tissue surrounding the blood vessels, hair roots and hair follicles and thereby enhancing blood flow to the follicles and hair root. However, through study and experimentation, the inventor came to appreciate that he was not fully realizing the benefit of the electrical stimulation.

As previously practiced, fluctuating current of 3–10 volts was generated across a pair of electrical contacts. One of the contacts was used as the massaging instrument and was encased in a padding of desired compressibility. The padding materials that were used were insulating materials and at least in part inhibited the flow of current. Yet a substantially stronger current could not feasibly be used.

As presently developed, an alternating electrical current results from a voltage between −0.250 and +1.350 volts across a pair of electrical contacts. Thus, the electrical impulse applied is generally a DC signal, but, because of the negative voltage excursions down to −0.250 volts, has some AC characteristics. In one embodiment, the contacts and padding have been modified so as to provide a compressible massaging pad that does not significantly inhibit the flow of current to the subject. Whereas padding materials are inherently current inhibiters, this problem was overcome by adopting highly conductive metal leads surrounded by cable shielding and encasing the contacts from the conductors in a highly absorbent padding material such as wool. The wool padding is moistened to render the wool padding conductive. In a second improved embodiment, the contacts are used without padding whereby a negative contact is surrounded by conductive gel and held in the person's hand while the positive electrode is applied directly, i.e., without intervening padding, to the site of massage.

As concerns the above second improved embodiment, another level of improvement is realized by producing the contacts using a three-fourth inch gold plated phonojack packed in silver solder. Such a structure allows optimum electrical surface contact and therefore less resistance. The contact thus constructed provides a sturdier contact and less chance of corrosion which would otherwise interfere with the variable low voltage electrical impulses.

A further modification is in the modified treatment. In the previous method, one of the contacts was utilized as the massaging instrument with the other contact placed on the scalp in close proximity to the area being massaged. The electrical current between the contacts was largely passed across the surface skin as distinguished from the sub-layers of skin. As previously discussed, the follicles, blood supply and connective tissue are located in the sub-layers of skin and limited benefit was being derived from the electrical stimulation.

In the present method, the ground contact is preferably held in the subject's hand thereby directing passage of the current down through the sub-layers of skin. The treatment is further improved by the structure of the silver solder encased gold plated phonojack in that the lower resistance between the contact and the subject means the subject can receive substantially the full range of low voltage electrical impulse.

The changes to the apparatus and method of U.S. Pat. No. 3,872,859 appear to have brought surprisingly improved results. Subjects believed to be experiencing slight rejuvenated hair growth are believed to experience greatly improved conditions associated with hair growth. Those that were believed to be experiencing hair loss retardation are believed to now be experiencing the condition associated with actual hair growth rejuvenation.

Although the theory has not been substantiated at present, it is also believed that administration of the treatment is enhanced by a perceived "operator feel". Operators utilizing the technique of the invention, experience a physical sense of increased resistance to the massaging action. This increased resistance is believed to occur in areas of taut skin and dense connective tissue. When not electrically stimulated, the entire scalp will seem to the operator to move at generally the same level of resistance. When stimulated by the electricity, there is a strong physical sensation that specific areas will not readily move under the massaging pad. It is theorized that the electrical impulse stimulation causes nerve-induced tightening of the connective tissue in those areas where the skin layers are already tight. The operator feels a more noticeable resistance to skin movement. These sensations were not being as frequently experienced under the prior method of the '859 patent and the resulting opportunity to focus treatment on the tight areas that are more readily sensed renders the treatment more effective. This sensation speeds up the effectiveness of the treatment which overcomes the otherwise ongoing deterioration of the scalp due to aging, heredity, and shape of skull.

The invention will be more fully understood by reference to the following detailed description and drawings.

DESCRIPTION OF THE DRAWINGS

FIG. 1 is a schematic illustration of the method and apparatus of the invention being applied to a subject person;

FIG. 2 is an enlarged partial view in section of the scalp of the subject person of FIG. 1 illustrating the treatment being applied to that person;

FIG. 3 is a further enlarged schematic illustration of what is believed to take place within the skin layers of the scalp during the treatment of FIGS. 1 and 2;

DETAILED DESCRIPTION OF THE INVENTION

Referring to FIG. 1, a subject person 10 is being treated in accordance with the invention. A low voltage generating device 12 includes a pair of electrical current conductors 14, 16 surrounded by cable shielding and terminating in contact pads 18, 20. The power source for the generating device 12 is 110 AC household current which is transformed by the generating device 12 into pulsating or oscillating DC current.

It is believed that the voltage should be continuously varied to achieve maximum results and thus the circuitry in the generating device 12 is designed to generate numerous square wave voltage configurations, e.g. as many as 12 square waves each of a different frequency. These are turned on and off at various intervals (timed) with the lower frequencies timed slower than the higher frequencies.

Twelve frequencies of the machine are as follows:

| | | |
|---|---|---|
| Channel One | 4,000 HZ Timed | 48 HZ Per Minute |
| Channel Two | 5,000 HZ Timed | 52 HZ Per Minute |
| Channel Three | 6,000 HZ Timed | 68 HZ Per Minute |
| Channel Four | 7,000 HZ Timed | 75 HZ Per Minute |
| Channel Five | 8,500 HZ Timed | 90 HZ Per Minute |
| Channel Six | 9,500 HZ Timed | 120 HZ Per Minute |
| Channel Seven | 10,500 HZ Timed | 140 HZ Per Minute |
| Channel Eight | 12,500 HZ Timed | 160 HZ Per Minute |
| Channel Nine | 14,500 HZ Timed | 185 HZ Per Minute |
| Channel Ten | 15,500 HZ Timed | 200 HZ Per Minute |
| Channel Eleven | 17,500 HZ Timed | 215 HZ Per Minute |
| Channel Twelve | 18,500 HZ Timed | 225 HZ Per Minute |

The output of the device is variable from −0.250 volt to approximately +1.350 volt.

Figure 4:
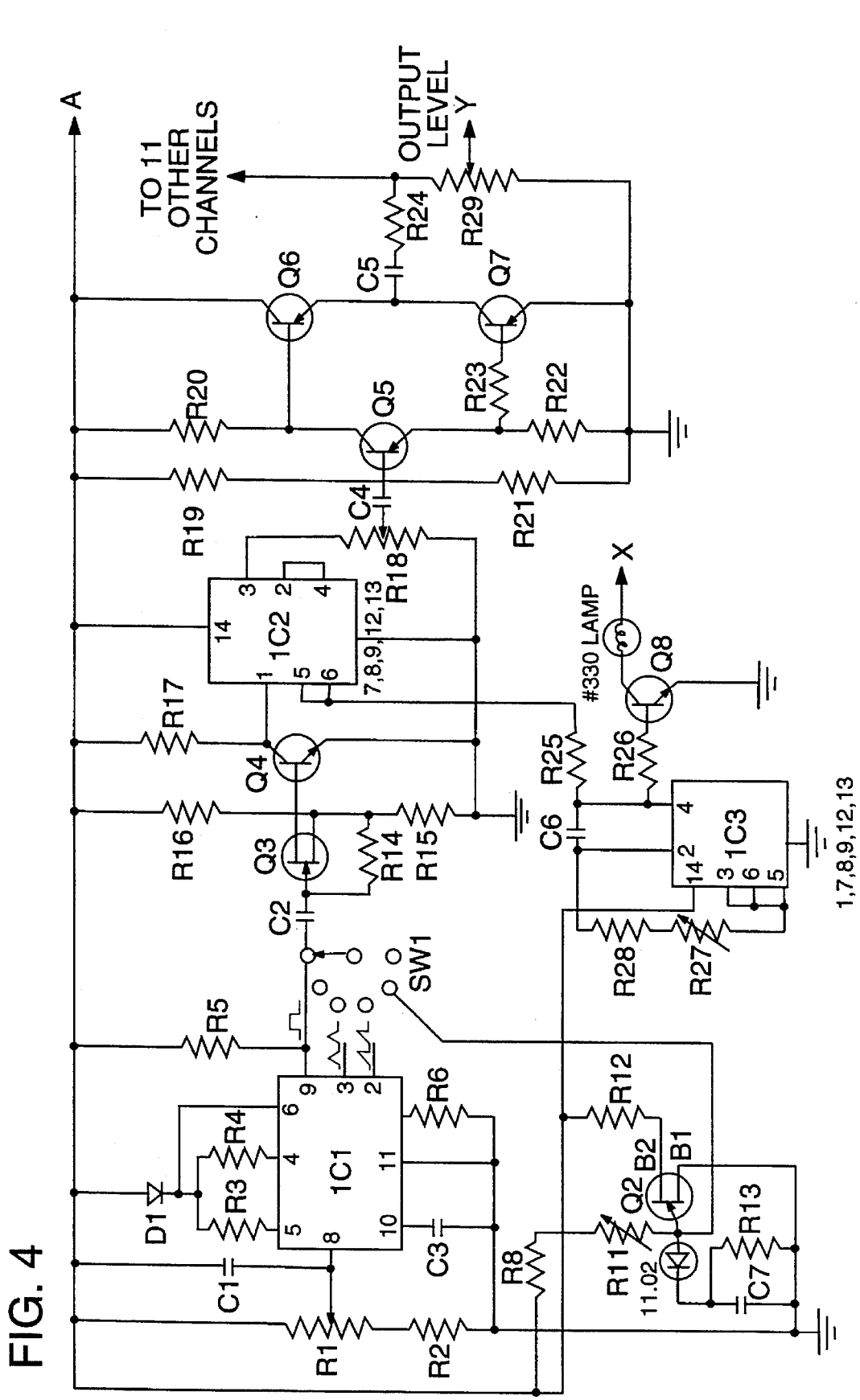
FIG. 4 is a circuit diagram for the voltage producing device utilized in the method and apparatus of FIG. 1.

One form of circuitry was disclosed in the prior U.S. Pat. No. 3,872,859. The preferred circuitry at present is illustrated in FIG. 4. A person skilled in electronics will have no problem in understanding the application of the circuitry of FIG. 4 and further description thereof is not deemed necessary and not explained in further detail.

Pad 18 is the ground terminal and completes the flow of electrical current being conveyed to the person's body from contact pad 20. The electrical current from pad 20 is passed into the subject person's scalp 30, down through the person's head 22, shoulder 24 and arm 26 to pad 18 which is being gripped by the person's hand 28.

Reference is now made to FIGS. 2 and 3 which schematically illustrate the treatment of the subject person's scalp 30 with the apparatus of the invention.

The various skin layers and connective tissue that make up the scalp are what is referred to as the scarf skin layer 32, the true skin layer 34, the adipose tissue layer 36, the galea layer 38, and the loose connected tissue layer 40. These skin layers overlie the skull 42. Embedded in the skin layers at the bottom of the true skin layer 34 is the hair follicle 44. Just below the follicle 44 are the blood vessels and arteries indicated generally by reference 46.

As explained in U.S. Pat. No. 3,872,859, the aging process causes a thickening and tightening of the skin layers, particularly the underlying galea layer 38 and loose connective tissue layer 40. This aging process tends to restrict blood flow and nerve action through the blood vessels and arteries which in turn causes a shrinking of the hair follicles. The shrinking or shortening of the follicles causes a withdrawal of the hair root and follicles from the blood vessels and arteries to further impede nourishment to the hair root and follicles. The gradual growth dormancy results in hair loss as previously explained.

Referring now to the treatment, it is the objective of the invention to cause a low voltage electrical variable impulse current to penetrate down through the skin layers and particulaneously down to the galea and connective tissue. Simultaneously, particularly where the operator is able to detect tightness of skin, the total skin thickness, i.e. all the skin layers, is "worked" to loosen the layers. Repeated massage and electrical impulse stimulation acts as nerve stimulation which facilitates a "reawakening" or reversal of the natural nutritional processes in the scalp which gradually cease to function properly, or on their own, over time-repeated treatment is utilized until the scalp regains its natural ability to "feed" the hair root and corresponding elongated hair follicle. The end result of this technique is that the scalp will be able to generate the condition associated with hair growth.

The present invention is a refinement of the apparatus and method of U.S. Pat. No. 3,872,859 and it is believed pertinent for the reader to understand the deficiencies of this prior method and apparatus in order to gain a full appreciation of the present invention.

The prior massaging process was not sufficiently localized. For the present invention, it is important that pressure be applied to a small area of the scalp which simulates a clamping of the skin to the skull. The contact pad is specifically designed to apply this localized pressure. In addition to the electrical stimulation, the pad is worked in a kneading action and from side to side but without moving the pad completely off the contacted surface of the skin. In response to the electrical stimulation and the working of the control pad, the underlying layers relax and move relative to the skull. Whereas it is believed the tightness is very much localized, the present refined method is believed to be far more effective than was the prior method of massage stimulation.

A second deficiency of the prior method is in the manner of electrically stimulating the scalp. The pair of contact pads were both placed on the scalp. The electrical current passing from one to the other was readily accomplished through the skin near the surface thereof. Whereas the tightness occurs in the deeper underlayers, the electrical stimulation was only partially effective. With the present invention, the ground contact is placed lower on the body so that the flow of electrical current is directed downward in the direction of shortest path connection, into and through the under layers of the skin. For convenience, the ground contact pad 18 is simply grasped by the subject person's hand 28 as illustrated in FIG. 1.

It is further believed that the prior apparatus was deficient in the way the contact pads were constructed. As explained in the prior patent, the electrical contact at the end of the electrical conductor was wrapped in conductive mesh, then in cotton batting and finally in cloth strips. The cotton batting and cloth strips were moistened so that the current from the mesh was conducted to the subject person's scalp. Two problems are believed to exist with this construction. First the mesh itself does not adequately conduct the electrical current from the end of the conductor to the cotton and cloth. Second the cotton does not retain moisture particularly well and rapidly dries out. What moisture is retained by the cotton is not spread evenly, i.e. the moisture settles in specified areas of the cotton and does not provide a reliable point-to-point conduction.

In the present invention, a highly conductive metal bulb 48 is connected to the conductor 52 within cable shielding 50. The bulb 48 has far greater surface area than the former wire conductor and transmits the current to the surrounding cloth material far better than the prior mesh. The bulb of the contact 20 is primarily copper coated with gold metal, or silver metal and then gold metal. The cloth material wrapped around the bulb 48 is wool. Wool has far better moisture retention and remains reliably conductive far longer than the cotton material of the prior apparatus. Bulb 48 of the ground contact 18 is preferably copper coated with silver metal, or coated with gold and then the silver metal. The outer coating of silver is preferred because experience has shown that gold is rubbed off due to handling by the subject person, whereas silver is still a good conductor and greater resistance to wear.

With the above refinement and the modification of the circuitry of apparatus 12 illustrated in FIG. 4, the method and apparatus as otherwise explained in U.S. Pat. No. 3,872,859 is generally applicable. The twelve square wave circuits generate a continually varying voltage of between −0.250 volt and +1.350 volt. The operator grasps the contact 20 and applies pressure against the scalp in the manner of FIGS. 1–3 as indicated by arrow 52, while the subject person holds the ground contact 18 as shown in FIG. 1. As indicated by arrow 54 in FIG. 3, the contact 20 is worked from side to side while maintaining pressure 52. This action is believed to far exceed the benefits of the method described in the prior patent. Furthermore, although applicant does not wish to be bound to this theory, there is a perceived feel of resistance to the working action at specific locations on the scalp which appears to be generated by the undesirable tight skin areas. This perception is prevalent with the voltage flowing to the skin as compared to when the current is turned off. It is believed that the skin reacts to the voltage causing it to tense or tighten. Where the underlayers have already tightened against the scalp, this tightening of the skin is magnified to the feel of tightness perceived by the operator. Thus, the electrical current is believed to provide a double benefit. First because the excitation coupled with "working" of the skin loosens the scalp, and second because the tight areas are more readily identified by the operator and the treatment can be focused on the areas of tight skin.

While the above-described method and apparatus has proven beneficial in most cases to improve conditions associated with stimulation of blood circulation and hair growth, certain difficult cases have not benefitted to as great an extent. An improved method and apparatus has been developed and will be now described which has proven successful not only in most cases, but also in those most extreme cases where stimulation of conditions associated with hair growth has been more difficult to achieve. FIGS. 5–8 illustrate the improvement of the method and apparatus relative to that of the above description.

Figure 5:
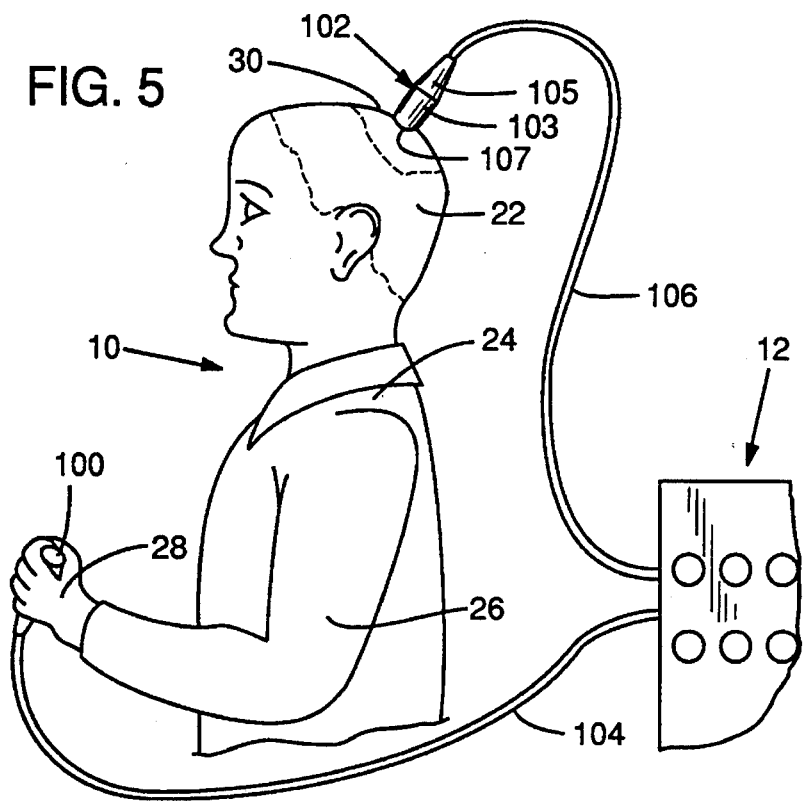
FIG. 5 is a schematic illustration of an improved method and apparatus of the invention being applied to a subject person.
Figure 6:
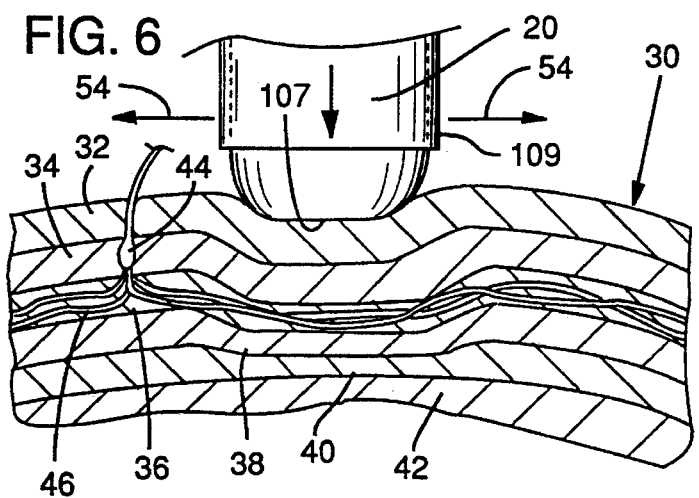
FIG. 6 is a detailed view of one electrode of FIG. 5 as applied to a person's scalp.
Figure 7:
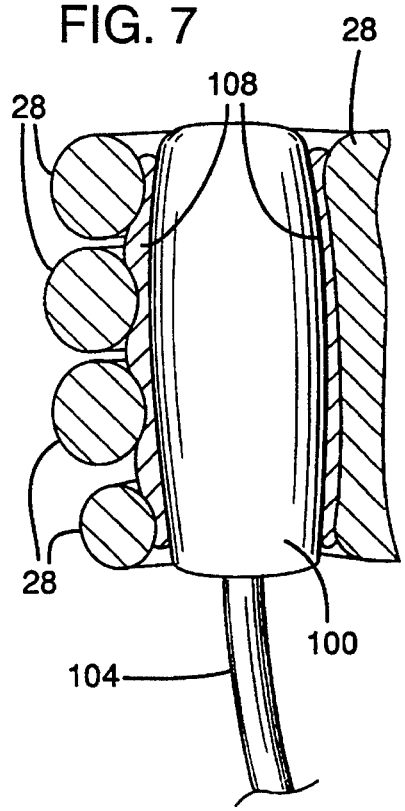
FIG. 7 is a detailed view of a second electrode of FIG. 5 as electrically coupled to the person's hand.

In FIG. 5, the device 12 is provided with modified electrodes 100 and 102. More particularly, each electrode 100 and 102 couples to the device 12 by way of corresponding electrical conductors 104 and 106, respectively. Each electrode 100 and 102 includes a copper bulb portion electrically coupled, e.g., by silver solder, to the corresponding conductor and driven by the device 12. Device 12 is operated as described above to provide a variety of output signals across the electrodes 100 and 102. The negative electrode 100 is held in the hand 28 and is surrounded by conductive gel 108 (FIG. 7) such as commonly used in the medical arts for procedures such as ultrasound imaging. The conductive gel 108 provides improved conductivity between the hand 28 and copper portion of electrode 100, and also breaks down skin resistance at hand 28. The prior method of using a moisture laden pad on a copper electrode with gold or silver plating produced undesirable resistance between the patient and the electrode and, therefore, reduced the effectiveness of the therapy.

Figure 10:
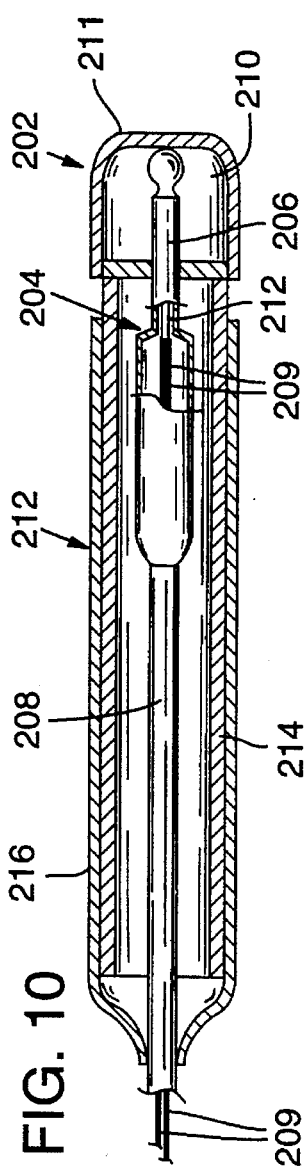
FIG. 10 is a detailed view of an improved electrode as applied to a person's scalp in the manner similar to that of FIG. 5.

The electrode 102 includes a copper head 103 coupled to conductor 106 and a handle 105. An insulating sleeve 109 (FIG. 6) surrounds most of electrode 102, with the exception of the smoothed distal end 107. FIG. 10 illustrates an improved electrode 202. Electrode 202 includes a phonojack 204 having a probe 206. The probe 206 is gold plated and encased in silver solder packing 210. A copper cap 211 fits over the solder and provides a smooth highly conductive surface that contacts the subject's skin. The phonojack 204 includes a double-shielded cable conductor 208 having conductor 209 with a copper wire solder connection 212 electrically connecting the conductor 209 to the probe 206. The end portion of the phonojack but not including the silver solder packing 210 is contained in a copper tubing 214 which is encased in an insulative shrink wrapping 216. The shrink wrapping 216 surrounding the copper tube 214 provides a handle to enable the operator to manipulate the electrode. The structure of FIG. 10 is considered optimal in its transmission of the electrical current and also is a sturdier form of construction. There is less chance of corrosion and the lower resistance means the client can receive the full range of low voltage electrical impulse.

Massage of scalp 30 by use of electrode 102 or 202 will now be described. The preferred method is with the person sitting in an upright position, the operator first massages the right top of the scalp and moves down to the right side of the head. Then, the operator massages the left top of the scalp and proceeds to the left side of the head followed by massage of the forehead area frontalis muscle. Massaging continues at the back of the head, first center to right then center to left. The person then lays face down for massaging the top and back of the head, and then the neck area and shoulder area for relaxation and stimulation. The person then lays on the left side and the operator massages the top, back and sides, finishing with the frontalis area. This procedure is then repeated with the person lying on the right side. The person is then placed on their back while the operator massages the top of the scalp sides and frontalis area. The treatment is then completed in an upright position with massaging of the top of the scalp, sides, back, frontalis area, and finishing with a massage of the neck and shoulder area. The preferred method can be varied to accommodate the necessary treatment.

Figure 8:
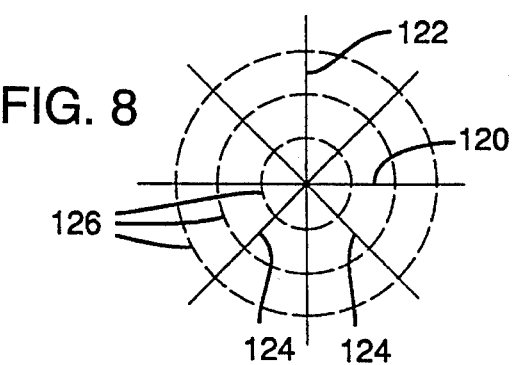
FIG. 8 illustrates a massage pattern according to the present invention.

While massaging with the electrode 102 or 202, the operator "works" the connective tissue overlying the scalp. Recall that several skin layers overly the connective tissue and these layers loosen far easier than the connective tissue. Thus, the operator in effect reaches down through the overlying layers by applying sufficient downward pressure to clamp the overlying layers to the connective tissue. He then applies moderate forward pressure and backs off of that forward pressure repetitively in the manner of a kneading action. The electrode pod is not moved off the overlying (skin and connective tissue) layers of the scalp during this process until, as a result of the tightness being released, there is a feel by the operator that the connective tissue has loosened. As the operator moves about different areas of the scalp, the electrode 102 or 202 is moved in a pattern such as illustrated in FIG. 8, i.e., first right to left along line 120, up and down along line 120, up and down along line 122 and then at 45 degrees along lines 124. Although described in connection with the scalp, the reader will understand that this same technique is applicable to other body portions.

The technique of the present invention allows the operator to penetrate deeper in a local area while providing greater awareness and control and, therefore, a more effective treatment. The improved apparatus and method described herein is believed to better loosen connective tissue about the skull and promote blood circulation with greater effectiveness, e.g., at deeper levels, then simple hand massage or mechanical massage which is believed to only effect the surface of the scalp or body area.

The loose connective tissue 40 next to the scalp must regain its elasticity for freedom of movement. Without this elasticity, muscles of the side of the head, back of the head and frontalis are restricted. Typically these muscles only move in one direction, e.g., with the sides, back and front of the head having all upwardly oriented movement. Releasing this unidirectional freedom of movement is believed to be extremely beneficial for nerve and blood circulation in these regions.

Following an initial massage according to the above-described method, wherein loosening of the skin is achieved, periodic follow-up maintenance treatments are suggested, e.g., about every two weeks to one month, are considered beneficial in maintaining the loosened condition of the connective tissue and, therefore, to improve the condition associated with hair growth. The length and frequency of each massage treatment is generally a function of the elastic quality of the subject's skin. Thus, prolonged treatments or more frequent treatments are applied to those persons exhibiting lesser elasticity.

Figure 9:
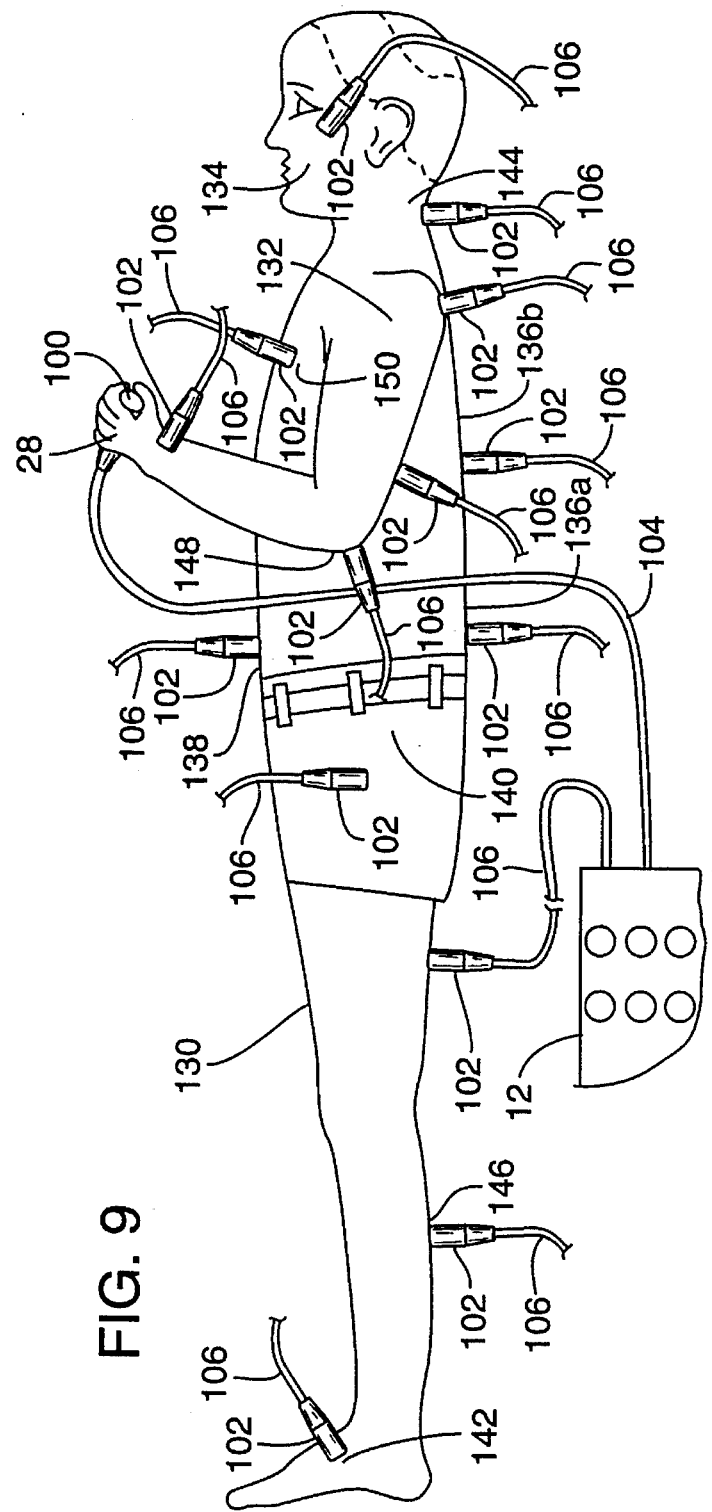
FIG. 9 illustrates body massage according to the present invention.

FIG. 9 illustrates use of the subject device for massaging generally other body portions, i.e., other than the scalp 30, as may be used in relief of arthritic conditions and other symptoms benefitted by use of electrical massage therapy. The particular body portions massaged in FIG. 9 shall not be considered a limitation in the broad variety of massage sites to which the device of the present invention may be applied. In FIG. 9, the person 10 holds the electrode 100 in the hand 28 as previously described with conductive gel 108 interposed there between to establish good electrical conductivity. The electrode 102 (which may instead be electrode 202) is illustrated as being applied to numerous other body portions such as the leg 130, shoulder 132, hand 28, face 134, torso 136 (e.g., lower back 136a and middle back 136b), abdomen 138, or hips 140. Other body portions whereat the massaging is known to have beneficial effects include the foot 142, neck 144, knee 146, elbow 148 and rib cage 150. However, this list is not exhaustive as virtually any part of the body may benefit including but not limited to, the face (jaw, forehead, chin), chest, arm, lung, stomach, heart, leg, ankle and hand. The use of electrical massage therapy according to the present invention generally provides improved blood circulation and loosening of connective tissue and is believed to provide agility in the person's skin and joints as well as relief of arthritic conditions.

The invention is not limited to the specific apparatus and method disclosed but instead encompasses the broader definition of the claims appended hereto.

I claim:

1. A method wherein an operator applies a massaging operation to a subject for loosening connective tissue of the subject having areas of undesired tightness that restricts the flow of blood through arteries and veins that are rooted in the connective tissue, said connective tissue underlying the skin surface of a designated body portion of a subject and separated from the skin surface by multiple skin layers, said method comprising:

positioning a pair of electrodes, a first electrode having a blunt contact surface held by and positioned by the operator on the skin surface of the designated body portion, said blunt contact surface when pressed against the skin surface by the operator being highly conductive of electrical current to said skin surface, and remotely positioning and independently securing a second electrode on the skin surface of a second body portion of the subject at a position remote from the position of the first electrode and not in contact with the operator, said second electrode being highly conductive of electrical current to the skin surface of said second body portion whereby a shortest path connection between the electrodes passes from one electrode to the other electrode in a path that extends down through the connective tissue of said designated body portion;

passing electrical current between said electrodes wherein said current is in the form of a low frequency wave with an electrical potential sufficient to stimulate the connective tissue underlying the first electrode; and systematically moving the first electrode by the operator from area to area on the designated body portion, and at each area clamping the electrode to the skin surface and moving the electrode and underlying skin layers relative to the body portion for determining areas of connective tissue tightness by the operator, and repetitively working the underlying skin areas of connective tissue tightness with said blunt contact surface of said first electrode pressed tightly to the skin by the operator for loosening connective tissue in the determined areas of tightness.

2. A method according to claim 1 wherein each of said electrodes include copper portions with the second electrode held in the subject's hand and a conductive gel interposed between the hand and the copper portion of said second electrode, and wherein the first electrode includes a copper portion applied directly in massaging fashion to the designated body portion.

3. A method according to claim 1 wherein said second electrode is electrically coupled at said subject's hand with conductive gel interposed between the second electrode and the subject's hand.

4. A method according to claim 1 wherein said first electrode is used to massage said designated body portion and said second electrode is electrically coupled at the hand of said subject with conductive gel interposed between the hand and said second electrode.

5. A method according to claim 1 wherein said designated body portion is at least one of a scalp, a leg, a face, a jaw, a shoulder, a torso, an abdomen, a hip, a neck, a chest, an arm, a hand, a foot, a knee and an ankle of said subject.

6. A method according to claim 1 wherein said designated body portion is a scalp portion overlying the skull portion of the subject, and wherein the step of systematically moving includes positioning said first electrode to a specific area of the scalp portion relative to the undesired tightness connective tissue resists movement relative to the subject's skull, and applying pressure thereto in a manner that produces a kneading motion with the electrode held in place relative to the skull portion until a release of the connective tissue tightness is detected, and moving the electrode from position to position in a close pattern surrounding said specific area of the body portion and repeating the process at each position for loosening the connective tissue in said body portion.

* * * * *